(12) United States Patent
Wright et al.

(10) Patent No.: US 10,633,689 B2
(45) Date of Patent: Apr. 28, 2020

(54) RAB ESCORT PROTEIN POTENCY ASSAY

(71) Applicant: Spark Therapeutics, Inc., Philadelphia, PA (US)

(72) Inventors: John Fraser Wright, Princeton, NJ (US); Marina Sumaroka, Philadelphia, PA (US)

(73) Assignee: SPARK THERAPEUTICS, INC., Philadelphia, PA (US)

( * ) Notice: Subject to any disclaimer, the term of this patent is extended or adjusted under 35 U.S.C. 154(b) by 66 days.

(21) Appl. No.: 15/806,136

(22) Filed: Nov. 7, 2017

(65) Prior Publication Data
US 2018/0135097 A1    May 17, 2018

Related U.S. Application Data

(60) Provisional application No. 62/418,637, filed on Nov. 7, 2016.

(51) Int. Cl.
*C12Q 1/48* (2006.01)

(52) U.S. Cl.
CPC .......... *C12Q 1/48* (2013.01); *C12Y 205/0106* (2013.01); *G01N 2333/91171* (2013.01)

(58) Field of Classification Search
None
See application file for complete search history.

(56) References Cited

U.S. PATENT DOCUMENTS

| 2014/0107185 A1 | 4/2014 | Maclaren et al. |
| 2016/0310618 A1 | 10/2016 | Hamel et al. |

OTHER PUBLICATIONS

Vasireddy et al in "AAV-Mediated Gene Therapy for Choroideremia: Preclinical Studies in Personalized Models" (PLOS One May 2013 vol. 8, No. 5, pp. 1-13. (Year: 2013).*
Vasireddy, et al., AAV-Mediated Gene Therapy for Choroideremia: Preclinical Studies in Personalized Models, PLoS One, 2013, 8(5)1-13, Article e61396.

* cited by examiner

*Primary Examiner* — Catherine S Hibbert
(74) *Attorney, Agent, or Firm* — Pillsbury Winthrop Shaw Pittman LLP

(57) ABSTRACT

Methods for measuring REP-1 and REP-2 activity are provided. In certain embodiments, a method includes: (a) contacting cells that do not express endogenous functional REP-1 or REP-2 protein with an adeno-associated viral (AAV) vector comprising a CHM gene encoding a REP-1 protein or CHM like gene encoding a REP-2 protein under conditions allowing cell transduction; (b) incubating transduced cells under conditions allowing expression of the encoded REP-1 or REP-2 protein; (c) lysing the transduced cells to produce an extract comprising the encoded REP-1 or REP-2 protein and Rab small GTPase (Rabs); (d) incubating said extract with a Rab substrate for a period of time and under conditions allowing prenylation of the Rab thereby forming prenylated Rab; and (e) detecting and/or quantifying the prenylated Rab, wherein the amount of prenylated Rab reflects REP-1 or REP-2 activity thereby measuring REP-1 or REP-2 activity.

32 Claims, 7 Drawing Sheets

Abbreviations:

REP — Rab Escort Protein (CHM/ CHM-like gene product)

Rab — Rab small GTPase

GDP — guanine diphosphate

RabGGTase — Rab geranyl geranyl transferase (two subunits: α and β)

CC — Cys – X – Cys motif (carboxy terminus of Rab)

GGPP — geranyl geranyl pyrophosphate

- In Rab prenylation, geranylgeranyl moieties are covalently attached to C-terminal cysteine residues on Rab via thioether bonds Simple Western size-based immunoassay Chemical structure of BGPP in comparison with natural substrate GGPP Prenylation Assay Legend:
1  HEK293 cells+ DMSO
2  HEK293 cells+ DMSO + SPK-CHM (MOI_1e5)
3  HEK293 cells+ 5uM Compactin (4 hours)

"B-GPP –" Control a - No compactin
b - Compactin 4 hours
c - Compactin overnight 4  HEK293 cells+ 5uM Compactin (4 hours) + SPK-CHM (MOI_1e5)
5  HEK293 cells+ 5uM Compactin (overnight)
6  HEK293 cells+ 5uM Compactin (overnight) + SPK-CHM (MOI_1e5)

RAB ESCORT PROTEIN POTENCY ASSAY

RELATED APPLICATION INFORMATION

This application claims priority to U.S. Provisional Patent Application No. 62/418,637, filed Nov. 7, 2016. The entire contents of the foregoing application is incorporated herein by reference, including all text, tables, sequence listing and drawings.

INTRODUCTION

Choroideremia is an X-linked monogenic disease caused by mutations in the CHM gene. The CHM gene encodes the Rab Escort Protein-1 (REP-1), which is 653 amino acids.

Mammals have a CHM-like gene that encodes REP-2, which compensates for absence of REP-1 in tissues other than the retina in Choroideremia patients.

Rab Escort Protein 1 (REP-1) has a role in intracellular trafficking. REP-1 facilitates post-translational lipid modification (prenylation) of Rab proteins, which are small GTPases and members of the Ras superfamily that play a key function in intracellular trafficking. REP-1 binds and coordinates interaction between newly synthesized Rab and RabGGTase, catalysing prenylation of Rab. REP-1 escorts prenylated Rab to target membrane. The Rab prenylation cycle is illustrated in FIG. 1.

The pathobiology in Choroideremia disease thought to be due to accumulation of unprenylated Rabs in retinal pigment epithelium (RPE) cells and/or related dysfunction in retina cell trafficking.

SUMMARY

The invention provides a Rab Escort Protein-1 (REP-1) potency assay. In one embodiment, the assay is an in vitro assay. In one embodiment, the assay is a cell based assay. In various embodiments, the cell based assay is in culture.

The invention also provides a Rab Escort Protein-2 (REP-2) potency assay. In one embodiment, the assay is an in vitro assay. In one embodiment, the assay is a cell based assay. In various embodiments, the cell based assay is in culture.

Representative cells appropriate for the assay include REP-1 negative RPE cells ($CHM^{neg}$). Representative control cells appropriate for the assay include REP-1 positive RPE cells ($CHM^{pos}$). In certain embodiments, REP-1 negative RPE cells ($CHM^{neg}$) comprise iPSC derived RPE cells (iPSC-RPE-$CHM^{neg}$). In certain embodiments, REP-1 positive RPE cells ($CHM^{pos}$) comprise iPSC derived RPE cells (iPSC-RPE-$CHM^{pos}$).

Cells appropriate for the assay (e.g., iPSC-RPE-$CHM^{neg}$) may be obtained from a Choroideremia patient. In addition, cells appropriate for the assay as a positive control (e.g., iPSC-RPE-$CHM^{pos}$) may be obtained from a patient that does not have Choroideremia. Such cells are typically human cells.

In certain embodiments, cells for the assay can be available from a cell bank or cell deposit which has REP-1 negative RPE cells (e.g., iPSC-RPE-$CHM^{neg}$) and REP-1 positive RPE cells (e.g., iPSC-RPE-$CHM^{pos}$) cells appropriate for the assay.

In other embodiments, cells appropriate for the assay are derived from blood cells, such as human blood cells. Blood cells of a Choroideremia patient can be used to generate iPS cells which in turn are differentiated to REP-1 negative RPE cells (iPSC-RPE-$CHM^{neg}$). Control REP-1 positive RPE cells (iPSC-RPE-$CHM^{pos}$) can be derived similarly from blood cells from a source that does not have Choroideremia, e.g., iPS cells are derived from a human subject from a human that does not have Choroideremia, and the iPS cells are in turn differentiated to REP-1 positive RPE cells (iPSC-RPE-$CHM^{pos}$).

In other embodiments, control REP-1 positive RPE cells (e.g., iPSC-RPE-$CHM^{pos}$) are derived from a Choroideremia patient ($CHM^{neg}$). The REP-1 negative RPE cells (e.g., iPSC-RPE-$CHM^{neg}$) can have the defective, non-functional or absent CHM gene replaced or supplemented (by way of transient or stable transfection) by a wild-type or other CHM like gene encoding functional REP-1 (or Rep-2) to generate control REP-1 positive RPE cells (e.g., iPSC-RPE-$CHM^{pos}$). Such transformed cells (from $CHM^{neg}$ to $CHM^{pos}$) only differ from the REP-1 negative RPE cells (e.g., iPSC-RPE-$CHM^{neg}$) in the CHM gene (e.g., iPSC-RPE-$CHM^{pos}$) thereby reducing artefacts potentially caused by heterogeneity in other genes/loci that occur naturally between different humans. Such gene replacement, correction or supplementation can be performed by various means, including but not limited to gene editing techniques such as Crispr/Cas-9, engineered Zinc Finger nucleases (ZFNs), delivered by way of vectors, viral vectors (e.g., AAV), nanoparticles, etc. CHM-gene-corrected iPS cells (e.g., iPSC-$CHM^{pos}$, which can be differentiated into control iPSC-RPE-$CHM^{pos}$ cells) or differentiated RPE cells (e.g., iPSC-RPE-$CHM^{pos}$) can be used as a positive isogenic control in prenylation The REP-1 negative RPE cells (e.g., iPSC-RPE-$CHM^{neg}$) and/or control REP-1 positive RPE cells (e.g., iPSC-RPE-$CHM^{pos}$) can be used for the potency assay as set forth herein. In addition, REP-1 negative RPE cells (e.g., iPSC-RPE-$CHM^{neg}$) and/or control REP-1 positive RPE cells (e.g., iPSC-RPE-$CHM^{pos}$) can be used as a source for a cell deposit or to establish a cell bank. Alternatively, REP-1 negative iPS cells or REP-1 positive iPS cells prior to their differentiation to RPE cells can be used as a source for a cell deposit or to establish a (frozen) cell bank, such that upon thawing from the bank, the iPS cells may be differentiated to RPE cells prior to use in the potency assay. Such deposited or banked cell lines can be stored at appropriate temperatures (e.g., liquid nitrogen, Liquid nitrogen storage around −190° C., or ultra low-temperature storage (e.g., about −70° C. and −80° C.) to preserve viability and optionally can be thawed and used as the source of cells provided for invention assays as set forth herein.

REP-1 negative RPE cells (e.g., iPSC-RPE-$CHM^{neg}$) can be transfected with a test CHM gene that encodes the Rab Escort Protein-1 (REP-1), and the encoded REP-1 can be analysed for activity. In particular embodiments, a vector is used to transfect cells with a test CHM gene that encodes the Rab Escort Protein-1 (REP-1). In certain embodiments, an adeno-associated virus (AAV) vector is used to transfect REP-1 negative RPE cells (e.g., iPSC-RPE-$CHM^{neg}$) with a test CHM gene that encodes the Rab Escort Protein-1 (REP-1).

Transfected REP-1 negative RPE cells (e.g., iPSC-RPE-$CHM^{neg}$) are analysed for REP-1 activity. In a particular embodiment. Rab prenylation activity is analysed. The activity can optionally be compared to a standard or threshold REP-1 activity, or activity of REP-1 in control REP-1 positive RPE cells (e.g., iPSC-RPE-$CHM^{pos}$).

REP-1 negative RPE cells (e.g., iPSC-RPE-$CHM^{neg}$) can be transfected over a range of vector (e.g. AAV) doses. Such a range of vector doses can be plotted as dose/activity to determine correlation between vector dose and REP-1 activity. The REP-1 activity can be compared to REP-1 activity of control REP-1 positive RPE cells (e.g., iPSC-RPE- CHM$^{pos}$) and identifying a vector dose that achieves comparable REP-1 activity. This can be used to determine differences in potency of different REP-1 proteins, lot variability/comparability, and whether a potency standard is met or not.

Prenylation of Rab can be detected by various means. For example, a labelled substrate (e.g., labelled geranylgeranyl diphosphate, or GGPP) can be used to detect and/or quantify Rab prenylation. Cell lysates comprising labelled Rab, extracts of labelled Rab, or purified or isolated labelled Rab, can be detected and/or quantified.

Substrates for prenylation of Rabs include detectably labelled geranylgeranyl diphosphate (GGPP). A radioactive label, such as tritium on a Rab substrate (e.g., tritiated [$^3$H]GGPP) can be detected by a scintillation counter, for example.

Substrates for prenylation of Rabs also include non-radioactive detectable labels. Accordingly, in various embodiments, the detectable label is not radioactivity, e.g., is not a radioactive isotope such as tritium ($^3$H).

A substrate can be biotinylated, such as BGPP, which can be detected and/or quantified by ELISA, mass spectrometry and/or Simple (e.g., automated) Western polypeptide size-based assays for example. Accordingly, in particular embodiments a detectable label facilitates detection and/or quantification without radioactivity, e.g., by an immunoassay such as Western blot, enzyme-linked immunosorbent assay (ELISA), mass spectrometry or by another assay such as Simple (e.g., automated) Western polypeptide size-based (WES) assay. In the example of biotin, detection and/or quantification can be by way of streptavidin-horseradish peroxidase (STR-HRP).

In certain embodiments, invention assays as disclosed herein are quantifiable, reproducible, they allow cross comparison between different Rab Escort Protein-1 analysed. In certain embodiments, invention assays as disclosed herein are suitable to meet stringent regulatory requirements in terms of lot consistency, clinical development and validation of Choroideremia therapies.

All of the foregoing embodiments applicable to REP-1 are also applicable to REP-2. For example, cells appropriate for a REP-2 potency assay include REP-2 negative RPE cells (CHM like$^{neg}$). Representative control cells appropriate for the assay include REP-2 positive RPE cells (CHM like$^{neg}$). In certain embodiments, REP-2 negative RPE cells (CHM like$^{neg}$) comprise iPSC derived RPE cells (iPSC-RPE-CHM like$^{neg}$). In certain embodiments, REP-2 positive RPE cells (CHM like$^{pos}$) comprise iPSC derived RPE cells (iPSC-RPE-CHM like$^{pos}$).

DETAILED DESCRIPTION

The invention provides methods for measuring and/or detecting prenylation activity and/or function. In various embodiments, the methods are specific and accurate. For example, the methods can be used to determine activity or function of a protein, such as Rep-1 and Rep-2, for various purposes including but not limited to measuring gene transfer efficiency, gene expression, activity or function of the protein, etc. Invention methods for measuring and/or detecting prenylation protein activity and/or function set forth herein include methods qualified for testing both drug substance (DS) and drug product (DP) in gene therapy applications.

Figure 7:
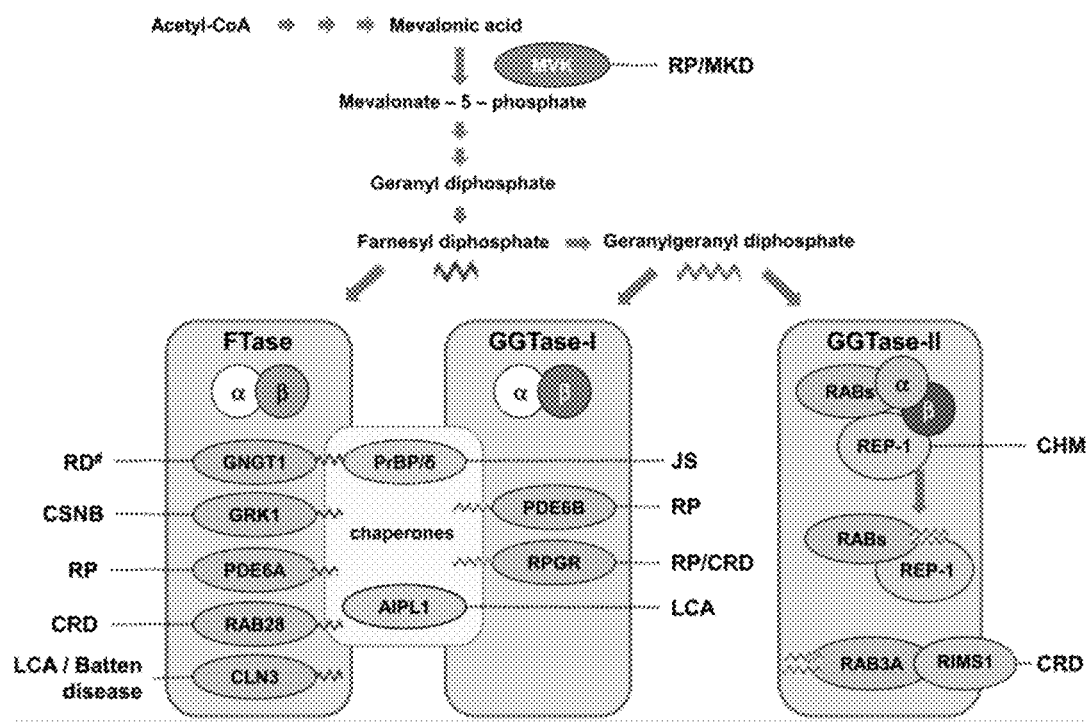
FIG. 7 shows a schematic representation of proteins that are prenylated and proteins that take part in prenylation process in the retina. Mutations in some of their corresponding genes were discovered to cause choroideremia (CHM), cone-rod dystrophy (CRD), congenital stationary night blindness (CSNB), Joubert syndrome (JS), Leber congenital amaurosis (LCA), mevalonate kinase deficiency (MKD), retinal disease (RD) and retinitis pigmentosa (RP). Proteins for which knockout mice displayed retinal disease are marked with a hash (#). α and β subunits of the prenylation enzymes encoded by different genes are depicted in different shades of grey.

Proteins suitable to be assayed according to the invention methods herein include Rab Escort Protein-1 (REP-1), which is 653 amino acids and Rab Escort Protein-2 (REP-2) which can compensate for absence of REP-1 in tissues other than the retina in Choroideremia patients. Additional proteins suitable according to the invention methods herein are set forth in FIG. 7 and described in Example 3.

iPS derived RPE cells can be produced as described in Nicolas Cereso, et al. (Molecular Therapy—Methods & Clinical Development (2014) 1, 14011; doi: 10.1038/mtm.2014.11); and Simona Torriano, et al. (Human Molecular Genetics. 26(18):3573-3584, September 2017). Other methods are suitable for obtaining RPE cells or deriving (differentiating) RPE cells from iPS cells.

The term "vector" refers to small carrier nucleic acid molecule, a plasmid, virus (e.g., AAV vector), or other vehicle that can be manipulated by insertion or incorporation of a nucleic acid. Vectors can be used for genetic manipulation (i.e., "cloning vectors"), to introduce/transfer polynucleotides into cells, and to transcribe or translate the inserted polynucleotide in cells. An "expression vector" is a vector that contains a gene or nucleic acid sequence with the necessary regulatory regions needed for expression in a host cell. A vector nucleic acid sequence generally contains at least an origin of replication for propagation in a cell and optionally additional elements, such as a Rep-1 or Rep-2 nucleic acid sequence, expression control element (e.g., a promoter, enhancer), intron, inverted terminal repeats (ITRs), optional selectable marker, polyadenylation signal.

An AAV vector is derived from adeno-associated virus. AAV vectors are useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous nucleic acid sequences (e.g., therapeutic proteins and agents) to human patients without causing substantial AAV pathogenesis or disease.

The term "recombinant," as a modifier of vector, such as rAAV vectors, as well as a modifier of sequences such as recombinant polynucleotides and polypeptides, means that the compositions have been manipulated (i.e., engineered) in a fashion that generally does not occur in nature. A particular example of a recombinant AAV vector would be where a nucleic acid, such as Rep-1 or Rep-2, that is not normally present in the wild-type AAV genome is inserted within the viral genome. Although the term "recombinant" is not always used herein in reference to AAV vectors, as well as sequences such as polynucleotides, recombinant forms including AAV vectors, polynucleotides, Rep-1, Rep-2, etc., are expressly included in spite of any such omission.

A "rAAV vector" is derived from the wild type genome of a virus, such as AAV by using molecular methods to remove the wild type genome from AAV genome, and replacing with a non-native (heterologous) nucleic acid, such as a nucleic acid encoding Rep-1 or Rep-2. Typically, for AAV one or both inverted terminal repeat (ITR) sequences of AAV genome are retained in the rAAV vector. A rAAV is distinguished from an AAV genome since all or a part of the AAV genome has been replaced with a non-native sequence with respect to the AAV genomic nucleic acid, such as with a heterologous nucleic acid encoding Rep-1 or Rep-2. Incorporation of a non-native sequence therefore defines the AAV as a "recombinant" AAV vector, which can be referred to as a "rAAV vector."

A recombinant AAV vector sequence can be packaged—referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV" or "rAAV particle" or "rAAV virion." Such rAAV, rAAV particles and rAAV virions include proteins that encapsidate or package the vector genome. Particular examples include in the case of AAV, capsid proteins.

A vector "genome" refers to the portion of the recombinant plasmid sequence that is ultimately packaged or encapsidated to form a rAAV particle. In cases where recombinant plasmids are used to construct or manufacture recombinant AAV vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into rAAV particles. Thus, a vector "genome" refers to the nucleic acid that is packaged or encapsidated by rAAV.

"AAV helper functions" refer to AAV-derived coding sequences (proteins) which can be expressed to provide AAV gene products and AAV vectors that, in turn, function in trans for productive AAV replication and packaging. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products (capsids) supply necessary packaging functions. AAV helper functions are used to complement AAV functions in trans that are missing from AAV vector genomes.

An "AAV helper construct" refers generally to a nucleic acid sequence that includes nucleotide sequences providing AAV functions deleted from an AAV vector which is to be used to produce a transducing AAV vector for delivery of a nucleic acid sequence of interest, by way of gene therapy to a subject, for example. AAV helper constructs are commonly used to provide transient expression of AAV rep and/or cap genes to complement missing AAV functions that are necessary for AAV vector replication. Helper constructs generally lack AAV ITRs and can neither replicate nor package themselves. AAV helper constructs can be in the form of a plasmid, phage, transposon, cosmid, virus, or virion. A number of AAV helper constructs have been described, such as plasmids pAAV/Ad and pIM29+45 which encode both Rep and Cap expression products (See, e.g., Samulski et al. (1989) J. Virol. 63:3822-3828; and McCarty et al. (1991) J. Virol. 65:2936-2945). A number of other vectors have been described which encode Rep and/or Cap expression products (See. e.g., U.S. Pat. Nos. 5,139,941 and 6,376,237).

The term "accessory functions" refers to non-AAV derived viral and/or cellular functions upon which AAV is dependent for replication. The term includes proteins and RNAs that are required in AAV replication, including moieties involved in activation of AAV gene transcription, stage specific AAV mRNA splicing, AAV DNA replication, synthesis of Cap expression products and AAV capsid packaging. Viral-based accessory functions can be derived from any of the known helper viruses such as adenovirus, herpesvirus (other than herpes simplex virus type-1) and vaccinia virus.

An "accessory function vector" refers generally to a nucleic acid molecule that includes polynucleotide sequences providing accessory functions. Such sequences can be on an accessory function vector, and transfected into a suitable host cell. The accessory function vector is capable of supporting rAAV virion production by the host cell. Accessory function vectors can be in the form of a plasmid, phage, transposon or cosmid. In addition, the full-complement of adenovirus genes are not required for accessory functions. For example, adenovirus mutants incapable of DNA replication and late gene synthesis have been reported to be permissive for AAV replication (Ito et al., (1970) J. Gen. Virol. 9:243; Ishibashi et al, (1971) Virology 45:317). Similarly, mutants within E2B and E3 regions have been shown to support AAV replication, indicating that the E2B and E3 regions are probably not involved in providing accessory functions (Carter et al., (1983) Virology 126:505).

Adenoviruses defective in the E1 region, or having a deleted E4 region, are unable to support AAV replication. Thus, E1A and E4 regions appear necessary for AAV replication, either directly or indirectly (Laughlin et al., (1982) J. Virol. 41:868; Janik et al., (1981) Proc. Natl. Acad. Sci. USA 78:1925; Carter et al., (1983) Virology 126:505). Other characterized Adenovirus mutants include: E1B (Laughlin et al. (1982), supra; Janik et al. (1981), supra; Ostrove et al., (1980) Virology 104:502); E2A (Handa et al., (1975) J. Gen. Virol. 29:239; Strauss et al., (1976) J. Virol. 17:140; Myers et al., (1980) J. Virol. 35:665; Jay et al., (1981) Proc. Natl. Acad. Sci. USA 78:2927; Myers et al., (1981) J. Biol. Chem. 256:567); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)). Studies of the accessory functions provided by adenoviruses having mutations in the E B coding region have produced conflicting results, but E1B55k may be required for AAV virion production, while E1B19k is not (Samulski et al., (1988) J. Virol. 62:206-210). In addition, International Publication WO 97/17458 and Matshushita et al., (1998) Gene Therapy 5:938-945, describe accessory function vectors encoding various Adenovirus genes. Exemplary accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such accessory function vectors are described, for example, in International Publication No. WO 01/83797.

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Cross-reactivity differences are usually due to differences in capsid protein sequences/antigenic determinants (e.g., due to VP1, VP2, and/or VP3 sequence differences of AAV serotypes).

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

rAAV vectors include any viral strain or serotype. As a non-limiting example, a rAAV plasmid or vector genome or particle (capsid protein) can be based upon any AAV serotype, such as AAV-1, -2, -3, -4, -5, -6, -7, -8, -9, -10, -11, for example. Such vectors can be based on the same of strain or serotype (or subgroup or variant), or be different from each other. As a non-limiting example, a rAAV plasmid or vector genome or particle (capsid) based upon one serotype genome can be identical to one or more of the capsid proteins that package the vector. In addition, a rAAV plasmid or vector genome can be based upon an AAV (e.g., AAV2) serotype genome distinct from one or more of the capsid proteins that package the vector genome, in which case at least one of the three capsid proteins could be a AAV1, AAV2, AAV3, AAV4, AAV5, AAV6, AAV7, AAV8, AAV9, AAV10, AAV11, or variant thereof, for example, rAAV vectors therefore include gene/protein sequences identical to gene/protein sequences characteristic for a particular serotype, as well as mixed serotypes.

In various exemplary embodiments, a rAAV vector includes or consists of a capsid sequence at least 70% or more (e.g., 75%, 80%, 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, or AAV11 capsid proteins. In various exemplary embodiments, a rAAV vector includes or consists of a sequence at least 70% or more (e.g., 75%, 80%, 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, or AAV11 inverted terminal repeats (ITRs).

rAAV, such as AAV1, AAV2, AAV3, AAV4, AAV5, AAV6, AAV7, AAV8, AAV9, AAV10, and AAV11, and variant, hybrid and chimeric sequences, can be constructed using recombinant techniques that are known to the skilled artisan, to include a heterologous polynucleotide (e.g., Rep-1 or Rep-2 sequence) flanked with one or more functional AAV ITR sequences. Such vectors have one or more of the wild type AAV genes deleted in whole or in part, but retain at least one functional flanking ITR sequence(s), as necessary for the rescue, replication, and packaging of the recombinant vector into a rAAV vector particle. A rAAV vector genome would therefore include sequences required in cis for replication and packaging (e.g., functional ITR sequences)

Methods are known in the art for generating rAAV virions. For example, transfection using AAV vector and AAV helper sequences in conjunction with coinfection with AAV helper viruses (e.g., adenovirus, herpesvirus, or vaccinia virus) or transfection with a recombinant AAV vector, an AAV helper vector, and an accessory function vector. Non-limiting methods for generating rAAV virions are described, for example, in U.S. Pat. Nos. 6,001,650 and 6,004,797. Following recombinant rAAV vector production (i.e. vector generation in cell culture systems), rAAV virions can be obtained from the host cells and cell culture supernatant and optionally purified.

The terms "nucleic acid" and "polynucleotide" are used interchangeably herein to refer to all forms of nucleic acid, oligonucleotides, including deoxyribonucleic acid (DNA) and ribonucleic acid (RNA). Nucleic acids include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Nucleic acids include naturally occurring, synthetic, and intentionally modified or altered polynucleotides. Nucleic acids can be single, double, or triplex, linear or circular, and can be of any length. In discussing nucleic acids, a sequence or structure of a particular polynucleotide may be described herein according to the convention of providing the sequence in the 5' to 3' direction.

A "host cell" denotes, for example, microorganisms, yeast cells, insect cells, and mammalian cells, that can be, or have been, used as recipients of an AAV vector plasmid, AAV helper construct, an accessory function vector, or other transfer DNA. The term includes the progeny of the original cell which has been transfected. Thus, a "host cell" generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. Exemplary host cells include human embryonic kidney (HEK) cells such as HEK293 cells.

A "transduced cell" is a cell into which a transgene (e.g., CHM or CHM like sequence) has been introduced. Accordingly, a "transduced" cell means a genetic change in a cell following incorporation of an exogenous molecule, for example, a nucleic acid (e.g., a transgene) into the cell. A "transduced" also includes progeny thereof. The cell(s) can be propagated (cultured) and the introduced protein (e.g., Rep-1 or Rep-2 protein) expressed, or vector, such as rAAV, produced by the cell. In the case of culture cells, nucleic acid sequences, such as a heterologous nucleic acid sequence, or plasmid or vector has been inserted into a chromosome can be maintained over the course of a plurality of cell passages.

A "cell line" refers to a population of cells capable of continuous or prolonged growth and division in vitro under appropriate culture conditions. Cell lines can, but need not be, clonal populations derived from a single progenitor cell. In cell lines, spontaneous or induced changes can occur in karyotype during storage or transfer of such clonal populations, as well as during prolonged passaging in tissue culture. Thus, progeny cells derived from the cell line may not be precisely identical to the ancestral cells or cultures. An exemplary cell line applicable to the invention activity methods is HEK293, such as HEK-LRAT cells.

An "expression control element" refers to nucleic acid sequence(s) that influence expression of an operably linked nucleic acid. Control elements, including expression control elements as set forth herein such as promoters and enhancers, rAAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of rAAV vectors, expression control elements will typically be within 1 to 1000 nucleotides from the transcribed nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence. A promoter typically increases an amount expressed from operably linked nucleic acid as compared to an amount expressed when no promoter exists.

An "enhancer" as used herein can refer to a sequence that is located adjacent to the nucleic acid sequence, such as selectable marker, or heterologous nucleic acid sequence Enhancer elements are typically located upstream of a promoter element but also function and can be located downstream of or within a sequence. Hence, an enhancer element can be located upstream or downstream, e.g., within 100 base pairs, 200 base pairs, or 300 or more base pairs of the as selectable marker, and/or a heterologous nucleic acid encoding a therapeutic protein or polynucleotide sequence. Enhancer elements typically increase expression of an operably linked nucleic acid above expression afforded by a promoter element.

The term "operably linked" means that the regulatory sequences necessary for expression of a nucleic acid sequence are placed in the appropriate positions relative to the sequence so as to effect expression of the nucleic acid sequence. This same definition is sometimes applied to the arrangement of nucleic acid sequences and transcription control elements (e.g. promoters, enhancers, and termination elements) in an expression vector, e.g., rAAV vector.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for vector packaging into a rAAV particle. In various embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., CHM or CHM like sequences, vectors, rAAV vectors, etc.) are an example of a genus of equivalent or similar features.

As used herein, the singular forms "a", "and," and "the" include plural referents unless the context clearly indicates otherwise. Thus, for example, reference to "an AAV vector," or "AAV particle," includes a plurality of such AAV vectors and AAV particles, and reference to "a cell" or "host cell" includes a plurality of cells and host cells.

The term "about" as used herein means values that are within 10% (plus or minus) of a reference value.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges are inclusive. Further, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLE 1

A Simple Western Assay is an example of an appropriated quantitative assay (WES). Variability in the manual processes that used to impact reproducibility, quantitation, time to result and overall data reliability is eliminated.

All assay steps are performed automatically including sample loading, size-based protein separation, immunoprobing or total protein labeling, washing, detection and data analysis. Separation and detection of proteins as small as 2 kDa or as large as 440 kDa can be performed in only 3 hours.

Sample data is displayed by lane in a virtual-blot like image as soon as the assay is completed. Quantitative results such as molecular weight, signal intensity (area), % area, and signal-to-noise for each immunodetected protein are presented in the results table automatically.

Figure 1:
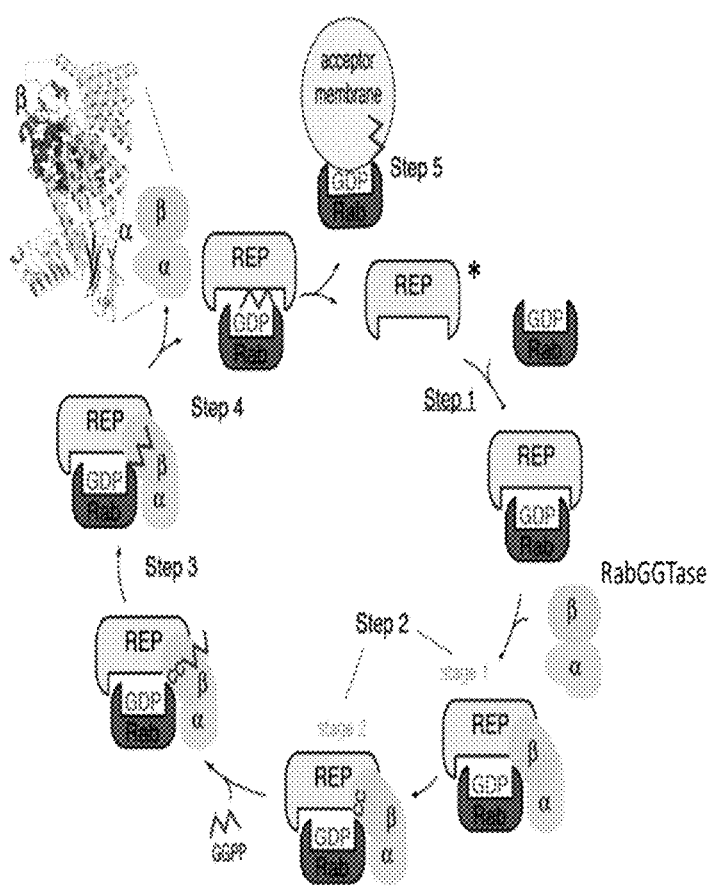
FIG. 1 shows Rabs prenylation cycle.
Figure 2:
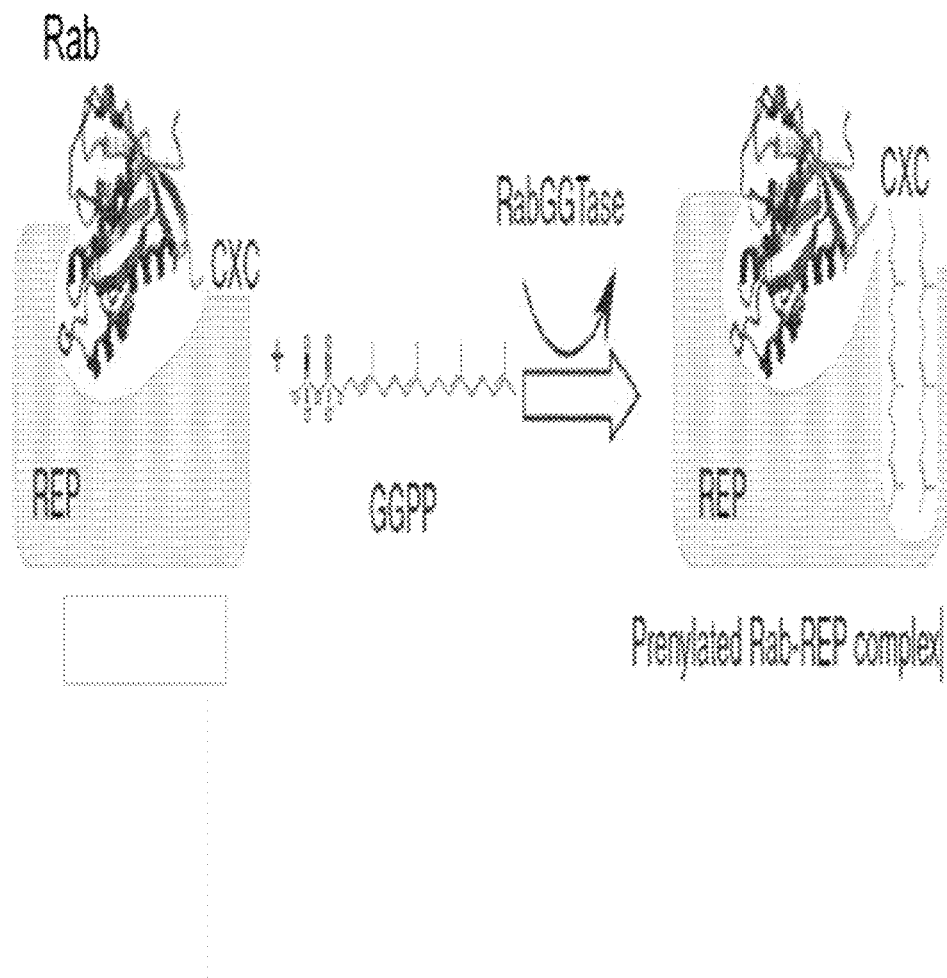
FIG. 2 shows Rabs prenylation thioester bond formation between Rab N-terminal Cys residues and GGPP.
Figure 3:
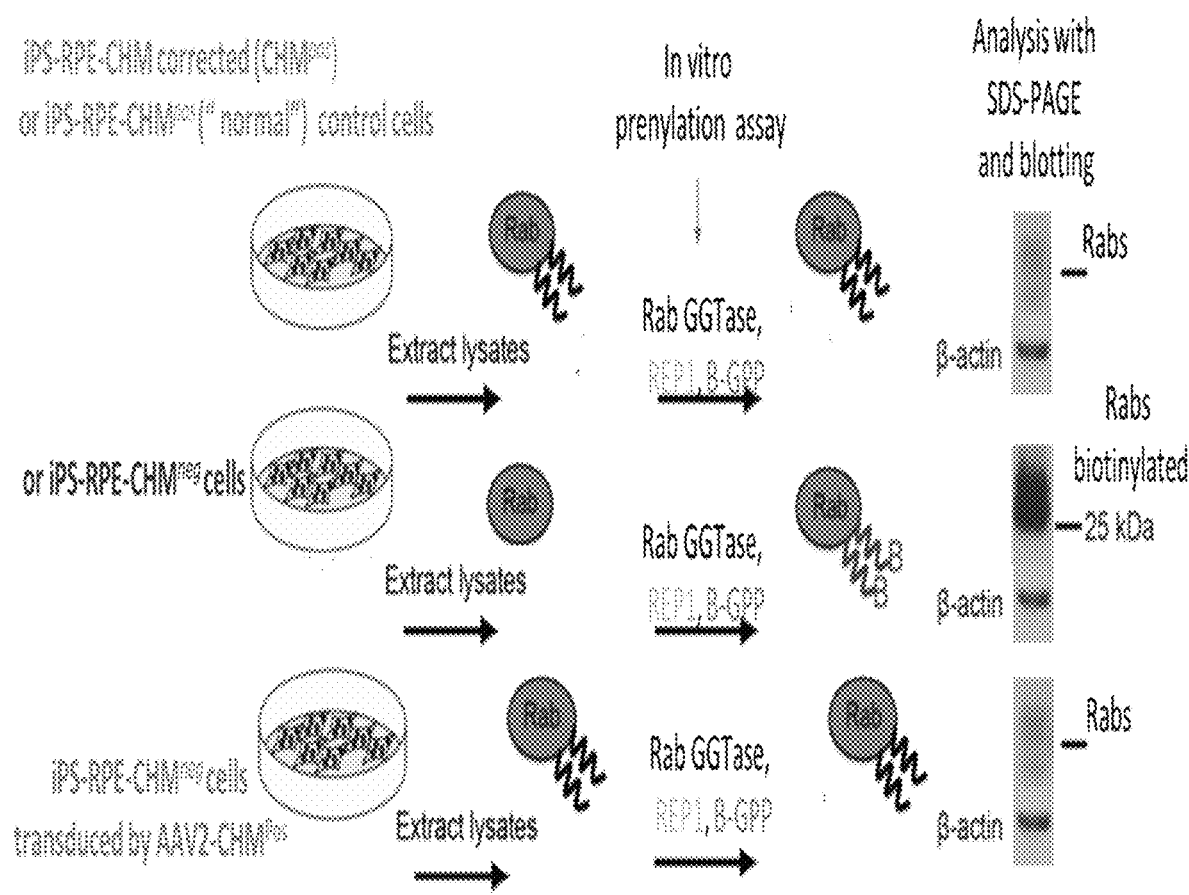
FIG. 3 shows a schematic representation of an exemplary invention potency assay.
Figure 4:
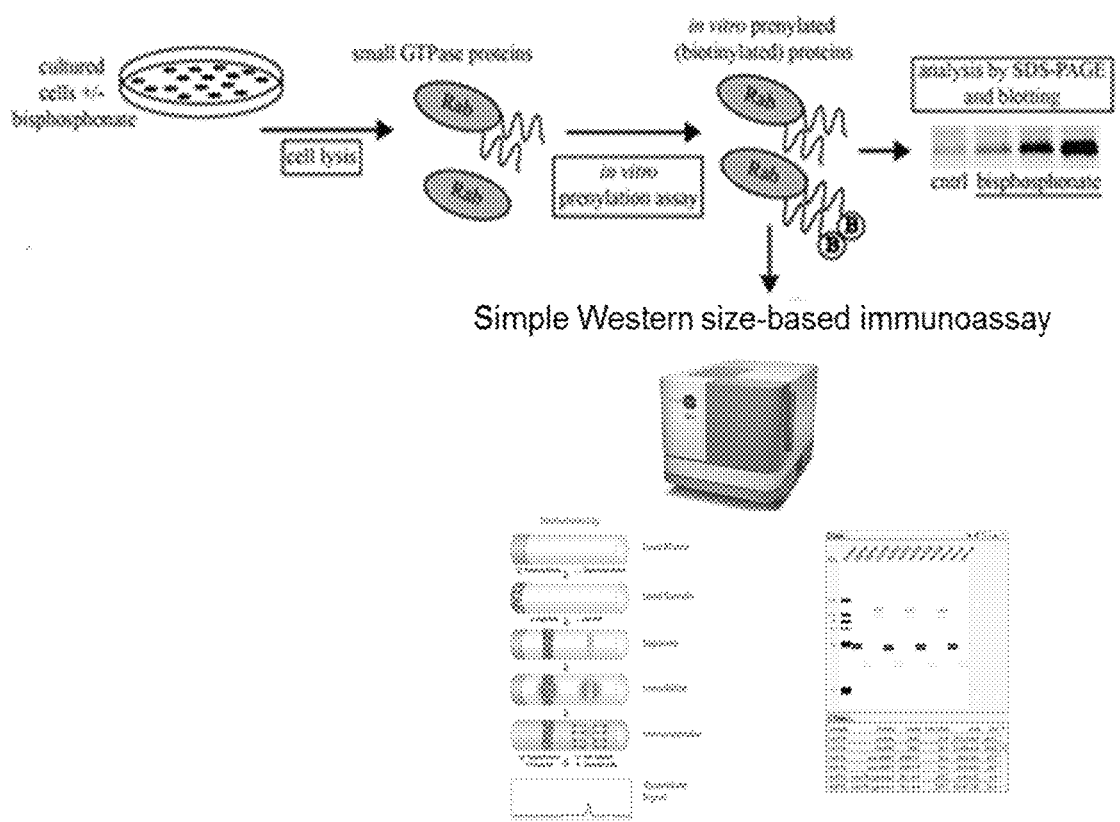
FIG. 4 shows a schematic representation of an exemplary invention potency assay.
Figure 4:
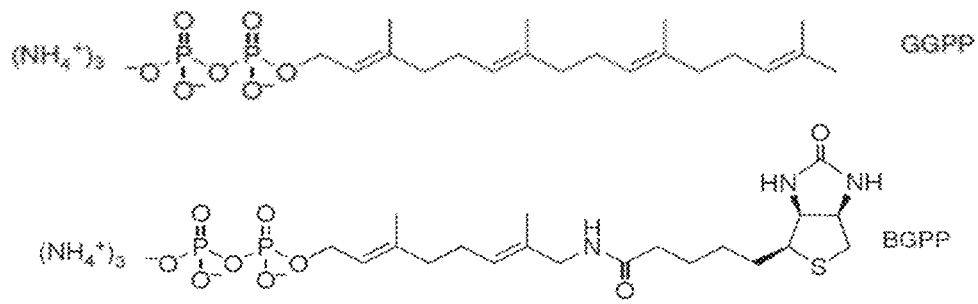

As illustrated in FIG. 4, as little as 40 nL of test cell lysate will be loaded into the WES apparatus. Proteins are automatically separated by size as they migrate through a stacking and separation matrix. Separated proteins will be then immobilized to the capillary wall via a photoactivated capture chemistry. Target REP-1 protein will be identified using a primary antibody and detected using an horse radish peroxidase (HRP)-conjugated secondary antibody. Biotinylated Rabs will be detected by chemiluminescence using Streptavidin-HRP. The resulting chemiluminescent signal will be detected and quantified.

EXAMPLE 2

Biotin incorporation was analyzed by using Streptavidin conjugated with DyLight 800. REP-1 expression was detected with Primary Anti-REP1-Antibody, clone 2F1 (MABN52), and Secondary Goat anti-Mouse IgG (H+L). Antibody, conjugated with DyLight 680. Only unprenylated Rabs were labelled in the in vitro prenylation assay and visualized as bands with molecular weight ~20-25 kDa. Immunoblots were scanned using Odyssey Infrared Imager (LiCOR).

Figure 5A:
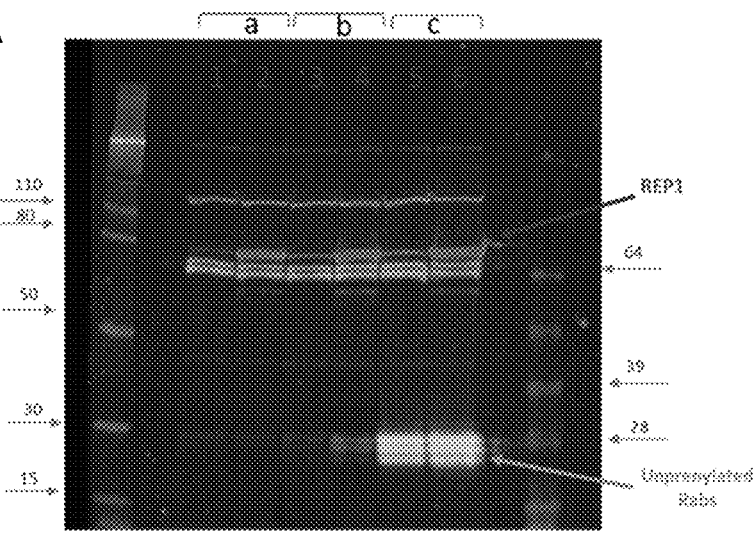
FIG. 5A shows an in vitro prenylation assay with biotin-geranyl-pyrophosphate (B-GPP) as a lipid donor followed by Western Blot analysis of HEK 293 cell lysates from untreated(a) and 5 μM Compactin treated (b, c) cells. REP1 expression and Rabs prenylation was analyzed in non-transduced HEK293 cells (lanes 1, 3, and 5) and after transduction of HEK293 cells with 100.000 vg/cell of AAV2 vector carrying a test CHM gene that encodes a Rab Escort Protein-1 (REP-1 or Rep-1) (lanes 2, 4, and 6).
Figure 5A:
Figure 5B:
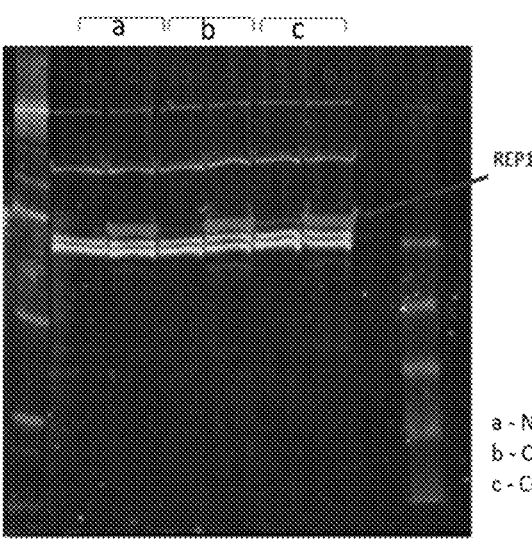
FIG. 5B shows an in vitro prenylation assay in the absence of biotin-geranyl-pyrophosphate (B-GPP) followed by Western Blot analysis of HEK 293 cell lysates from untreated(a) and Compactin (5 μM) treated (b, c) cells. (Negative control)
Figure 5B:

Faint bands of endogenous REP-1 (~75-80 kDa, REP 1 arrow) were detected in the untreated and compactin-treated lysates of non-transduced HEK293 cells (FIG. 5A, lanes 1, 3, and 5). The level of REP1 expression was significantly higher in HEK293 cells transduced with AAV2 vector carrying a test CHM gene that encodes Rab Escort Protein-1 (REP-1) under control of a chicken-beta actin (CBA) promoter (AAV2-CHM vector) (FIG. 5A, lanes 2, 4, and 6). Unprenylated Rabs (indicated by the other arrow) were clearly observed in the compactin-treated cells without (FIG. 5A, lane 5) and with transduction by AAV2 vector carrying a test CHM gene that encodes Rab Escort Protein-1 (REP-1) (FIG. 5A, lane 6). No difference in prenylation was observed in HEK 293 cells without compactin treatment (FIG. 5A, lanes 1 and 2). For the negative control, in vitro prenylated Rabs were observed (FIG. 5B).

The same prenylation assay was performed on iPSC-CHM$^{pos}$, iPSC-CHM$^{neg}$ cells grown on feeder cells and on iPSC-CHM cells without feeder cells.

Figure 6A:
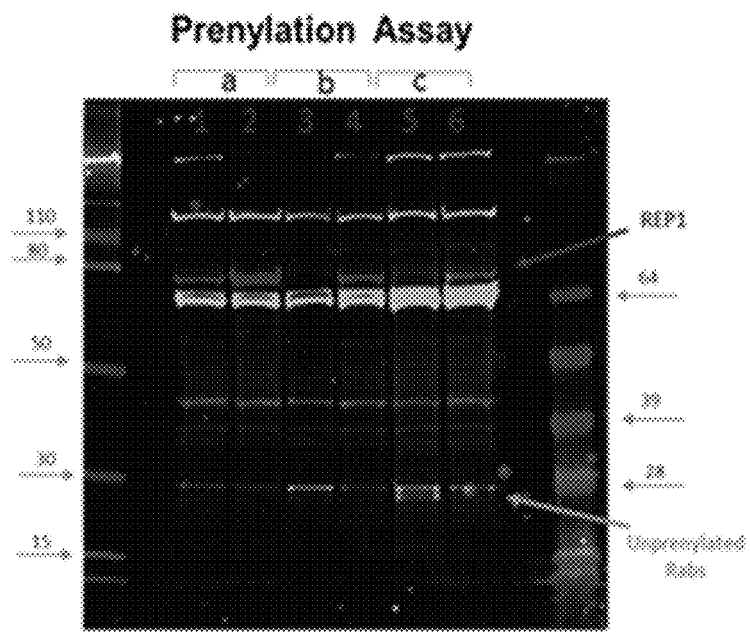
FIG. 6A shows a western blot analysis of REP1 expression and Rabs prenylation performed on iPSC-CHM$^{pos}$ (a), iPSC-CHM$^{neg}$ cells growing on feeder cells (MEFs)(b) and iPSC-CHM$^{neg}$ feeder free cells(c) after in vitro prenylation assay with biotin-geranyl-pyrophosphate (B-GPP) as a lipid donor. Assay was performed on non-transduced iPSCs (lanes 1, 3 and 5) and iPSCs transduced with AAV2 vector carrying a test CHM gene that encodes a Rab Escort Protein-1 (REP-1).

FIG. 6A. Lanes 1, 3 and 5 represent cell lysates from non-transduced cells.

FIG. 6A, Lanes 2, 4 and 6 represent lysates from cells transduced with 100.000 vg/cell of AAV2 vector carrying a CHM expression cassette encoding Rab Escort Protein-1 (REP-1).

Figure 6B:
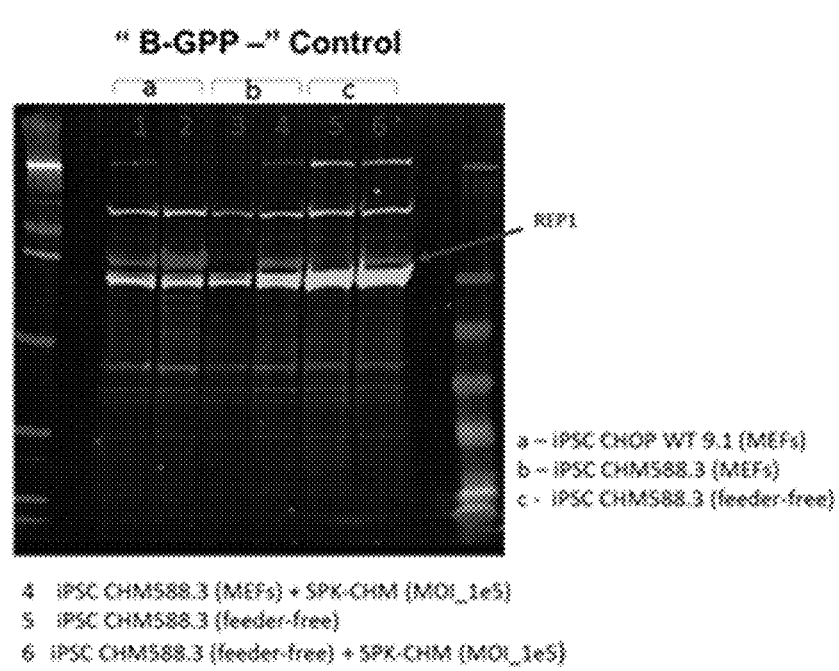
FIG. 6B shows a western blot analysis of REP1 expression and Rabs prenylation performed on iPSC-CHM$^{pos}$ (a), iPSC-CHM$^{neg}$ cells growing on a feeder cells (MEFs)(b) and on iPSC-CHM$^{neg}$ feeder free cells(c) after in vitro prenylation assay in the absence of biotin-geranyl-pyrophosphate (B-GPP) as a lipid donor (Negative control).

An ~75-80 kDa band (REP 1, arrow) corresponding to REP1 is clearly visualized in non-transduced iPSC-CHM$^{pos}$ cells (FIG. 6A, lane 1) and in transduced iPSC-CHM$^{pos}$ cells (FIG. 6A, lane 2). REP-1 expression is not detectable in the non-transduced iPSC-CHM$^{neg}$ cells (FIG. 6A, lanes 3 and 5), but can be observed in the iPSC-CHM$^{neg}$ cells transduced with AAV2 vector carrying a CHM expression cassette encoding REP-1. (FIG. 6A, lanes 4 and 6). Level of unprenylated Rabs (arrow) is reduced in iPSC-CHM$^{neg}$ cells transduced with AAV2 vector carrying a CHM expression cassette encoding the Rab Escort Protein-1 (REP-1). (FIG. 6A, lanes 4 and 6). For the negative control, in vitro prenylated Rabs were observed (FIG. 6B).

EXAMPLE 3

The prenylation potency assay exemplified herein for Rep-1 and Rab proteins in RPE cells can also be used for other proteins (e.g. Rep-2) that are crucial in the prenylation process or are key substrates for prenylation (approximately 70 Rab proteins that have been described) in RPE and other cells types. For example, mutations in the retina in other corresponding genes were discovered to cause cone-rod dystrophy (CRD), congenital stationary night blindness (CSNB), Joubert Syndrome (JS), Leber Congenital Amaurosis (LCA), Mevalonate Kinase Deficiency (MKD), Retinal Disease (RD) and Retinitis Pigmentosa (RP).

Table of Exemplary Rab proteins

| Name | Subcellular location |
| --- | --- |
| RAB1 (Ypt1, RabO) | Golgi complex |
| RAB2 | ER, cis-Golgi network |
| RAB3A | secretory and synaptic vesicles |
| RAB4 | recycling endosomes |
| RAB5A | clathrin-coated vesicles, plasma membranes |
| RAB5C (Vps21, RabB) | early endosomes |
| RAB6 (Ypt6, RabC) | Golgi and trans-Golgi network |
| RAB7 (Ypt7, RabS) | late endosomes, vacuoles |
| RAB8 | basolateral secretory vesicles |
| RAB9 | late endosome, trans-golgi network |
| RAB11 (Ypt31, RabE) | recycling endosomes, post-Golgi exocytic carriers |
| RAB14 | early endosomes |
| RAB18 | lipid droplets, golgi, endoplasmic reticulum |
| RAB25 | small-scale transport, promoter for tumor development[9] |
| RAB39a | binds Caspase-1 in inflammasome |
| SEC4 | secretory vesicles |

What is claimed is:

1. A method for measuring REP-1 activity comprising:
   (a) contacting REP-1 negative RPE cells (CHMneg) that do not express endogenous functional REP-1 protein with an adeno-associated viral (AAV) vector comprising a CHM gene encoding a REP-1 protein under conditions allowing cell transduction;
   (b) incubating transduced cells under conditions allowing expression of the encoded REP-1 protein;
   (c) lysing the transduced cells to produce an extract comprising the encoded REP-1 protein and Rab small GTPase (Rabs);
   (d) incubating said extract with a Rab substrate for a period of time and under conditions allowing prenylation of the Rab thereby forming prenylated Rab; and
   (e) detecting and/or quantifying the prenylated Rab, wherein the amount of prenylated Rab reflects REP-1 activity thereby measuring REP-1 activity.

2. The method of claim 1, wherein the REP-1 protein is mammalian.

3. The method of claim 1, wherein the REP-1 protein comprises human REP-1.

4. The method of any of claims 1-3, wherein the cells comprise Human REP-1 negative RPE cells (CHMneg).

5. The method of any of claims 1-3, wherein the cells express REP-1 stably or transiently.

6. The method of any of claims 1-3, wherein the Rab substrate comprises a geranyl moiety.

7. The method of any of claims 1-3, wherein the Rab substrate is detectably labelled.

8. The method of any of claims 1-3, wherein the Rab substrate is non-radioactively labelled.

9. The method of any of claims 1-3, wherein the Rab substrate is radioactively labelled.

10. The method of any of claims 1-3, wherein the Rab substrate is GGPP.

11. The method of any of claims 1-3, wherein the Rab substrate comprises a biotinylated geranyl moiety.

12. The method of any of claims 1-3, wherein the Rab substrate comprises BGPP.

13. The method of any of claims 1-3, wherein step (c) further comprises isolating or purifying Rab from the extract.

14. The method of any of claims 1-3, wherein step (d) or (e) further comprises isolating or purifying the prenylated Rab.

15. The method of any of claims 1-3, wherein the prenylated Rab is detected and/or quantified via a detectable label.

16. The method of any of claims 1-3, wherein the prenylated Rab is detected and/or quantified via a non-radioactive detectable label.

17. The method of any of claims 1-3, wherein the prenylated Rab is detected and/or quantified via ELISA.

18. The method of any of claims 1-3, wherein the prenylated Rab is detected and/or quantified via western blotting or a Western polypeptide size-based (WES) assay.

19. The method of any of claims 1-3, wherein the prenylated Rab is detected and/or quantified via mass spectrometry.

20. The method of any of claims 1-3, wherein the prenylated Rab is detected and/or quantified via a radioactive detectable label.

21. The method of any of claims 1-3, further comprising comparing the REP-1 activity to REP-1 activity of control REP-1 positive cells (CHMpos).

22. The method of any of claims 1-3, further comprising comparing the REP-1 activity to REP-1 activity of control REP-1 positive RPE cells (CHMpos).

23. The method of any of claims 1-3, wherein the cells are derived or obtained from a patient having Choroideremia.

24. The method of any of claims 1-3, wherein the cells are derived from iPS cells obtained from a patient having Choroideremia.

25. The method of claim 21, wherein the control REP-1 positive cells (CHMpos) are obtained or derived from a subject that does not have Choroideremia.

26. The method of claim 21, wherein the control REP-1 positive cells (CHMpos) are derived from iPS cells obtained from a subject that does not have Choroideremia.

27. The method of claim 21, wherein the control REP-1 positive cells (CHMpos) are obtained or derived from a subject that that has Choroideremia and said control cells have been stably or transiently transduced with a CHM gene that encodes REP-1.

28. The method of claim 21, wherein the control REP-1 positive cells (CHMpos) are derived from iPS cells obtained from a subject that has Choroideremia and said control cells or iPS cells have been stably or transiently transduced with a CHM gene that encodes REP-1.

29. The method of claim 4, wherein the REP-1 negative RPE cells comprise iPSC-RPE-CHMneg cells.

30. The method of claim 21, wherein the REP-1 positive RPE cells comprise iPSC-RPE-CHMpos cells.

31. The method of claim 1, wherein the adeno-associated viral (AAV) vector comprises a capsid protein sequence or inverted terminal repeat sequence having 70% or more sequence identity to a capsid protein sequence or to an inverted terminal repeat sequence of any serotype selected from AAV1, AAV2, AAV3, AAV4, AAV5, AAV6, AAV7, AAV8, AAV9, and AAV10.

32. The method of claim 1, wherein the adeno-associated viral (AAV) vector comprises a capsid protein or inverted terminal repeat of any serotype selected from AAV1, AAV2, AAV3, AAV4, AAV5, AAV6, AAV7, AAV8, AAV9, AAV10.

* * * * *